(12) United States Patent
Graham et al.

(10) Patent No.: US 9,623,162 B2
(45) Date of Patent: Apr. 18, 2017

(54) IMPLANTABLE BLOOD PUMP

(71) Applicant: RELIANTHEART, INC., Houston, TX (US)

(72) Inventors: William C. Graham, Houston, TX (US); Frederick D. Swain, Houston, TX (US); Anthony Williams, Houston, TX (US); Bryan E. Lynch, Houston, TX (US); Rodger G. Ford, Tucson, AZ (US); Sailesh Saxena, Bellaire, TX (US)

(73) Assignee: RELIANTHEART INC., Houston, TX (US)

( * ) Notice: Subject to any disclaimer, the term of this patent is extended or adjusted under 35 U.S.C. 154(b) by 0 days.

(21) Appl. No.: 14/926,403

(22) Filed: Oct. 29, 2015

(65) Prior Publication Data

US 2016/0228629 A1 Aug. 11, 2016

Related U.S. Application Data

(60) Provisional application No. 62/075,858, filed on Nov. 5, 2014.

(51) Int. Cl.
*A61N 1/362* (2006.01)
*A61M 1/12* (2006.01)
*A61M 1/10* (2006.01)

(52) U.S. Cl.
CPC ............ *A61M 1/122* (2014.02); *A61M 1/101* (2013.01)

(58) Field of Classification Search
CPC ....... A61M 1/122; A61M 1/10; A61M 1/1036
See application file for complete search history.

(56) References Cited

U.S. PATENT DOCUMENTS

| 5,527,159 | A | 6/1996 | Bozeman, Jr. et al. |
| 5,947,892 | A | 9/1999 | Benkowski et al. |
| 5,957,672 | A | 9/1999 | Aber |
| 2003/0193252 | A1* | 10/2003 | Locke ................... A61M 1/101 310/90.5 |
| 2005/0008496 | A1* | 1/2005 | Tsubouchi ............ A61M 1/101 417/44.2 |

* cited by examiner

*Primary Examiner* — Robert N Wieland
(74) *Attorney, Agent, or Firm* — Sutton McAughan Deaver PLLC

(57) ABSTRACT

A blood pump having a rotor and a stator, in which the rotor has a filled core channel and a plurality of filled radial channels configured to maximize the communication of magnetic flux.

19 Claims, 4 Drawing Sheets

IMPLANTABLE BLOOD PUMP

CROSS REFERENCE TO RELATED APPLICATIONS

This application is a non-provisional, and claims priority benefit, of U.S. Application Serial No. 62/075,858, filed Nov. 5, 2014, entitled "Implantable Blood Pump", which is incorporated herein by specific reference.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The present inventions relate generally to implantable blood pumps, and more specifically, the present inventions relate to ventricular assist blood pumps.

Description of the Related Art

U.S. Pat. No. 5,527,159 purportedly discloses, "A rotary blood pump includes a pump housing for receiving a flow straightener, a rotor mounted on rotor bearings and having an inducer portion and an impeller portion, and a diffuser. The entrance angle, outlet angle, axial and radial clearances of blades associated with the flow straightener, inducer portion, impeller portion and diffuser are optimized to minimize hemolysis while maintaining pump efficiency. The rotor bearing includes a bearing chamber that is filled with cross-linked blood or other bio-compatible material. A back emf integrated circuit regulates rotor operation and a microcomputer may be used to control one or more back emf integrated circuits. A plurality of magnets are disposed in each of a plurality of impeller blades with a small air gap. A stator may be axially adjusted on the pump housing to absorb bearing load and maximize pump efficiency."

U.S. Pat. No. 5,947,892 purportedly discloses "A blood pump that comprises a pump housing having a blood flow path therethrough, a blood inlet, and a blood outlet; a stator mounted to the pump housing, the stator having a stator field winding for producing a stator magnetic field; a flow straightener located within the pump housing, and comprising a flow straightener hub and at least one flow straightener blade attached to the flow straightener hub; a rotor mounted within the pump housing for rotation in response to the stator magnetic field, the rotor comprising an inducer and an impeller; the inducer being located downstream of the flow straightener, and comprising an inducer hub and at least one inducer blade attached to the inducer hub; the impeller being located downstream of the inducer, and comprising an impeller hub and at least one impeller blade attached to the impeller hub; and preferably also is comprising a diffuser downstream of the impeller, the diffuser comprising a diffuser hub and at least one diffuser blade. Blood flow stagnation and clot formation within the pump are minimized by, among other things, providing the inducer hub with a diameter greater than the diameter of the flow straightener hub; by optimizing the axial spacing between the flow straightener hub and the inducer hub, and between the impeller hub and the diffuser hub; by optimizing the inlet angle of the diffuser blades; and by providing fillets or curved transitions between the upstream end of the inducer hub and the shaft mounted therein, and between the impeller hub and the shaft mounted therein."

U.S. Pat. No. 5,957,672 purportedly discloses "Methods and apparatus [] for a blood pump bearing system within a pump housing to support long-term high-speed rotation of a rotor with an impeller blade having a plurality of individual magnets disposed thereon to provide a small radial air gap between the magnets and a stator of less than 0.025 inches. The bearing system may be mounted within a flow straightener, diffuser, or other pump element to support the shaft of a pump rotor. The bearing system includes a zirconia shaft having a radiused end. The radiused end has a first radius selected to be about three times greater than the radius of the zirconia shaft. The radiused end of the zirconia shaft engages a flat sapphire endstone. Due to the relative hardness of these materials a flat is quickly produced during break-in on the zirconia radiused end of precisely the size necessary to support thrust loads whereupon wear substantially ceases. Due to the selection of the first radius, the change in shaft end-play during pump break-in is limited to a total desired end-play of less than about 0.010 inches. Radial loads are supported by an olive hole ring jewel that makes near line contact around the circumference of the shaft to support high speed rotation with little friction. The width of olive hole ring jewel is small to allow heat to conduct through to thereby prevent heat build-up in the bearing. A void defined by the bearing elements may fill with blood that then coagulates within the void. The coagulated blood is then conformed to the shape of the bearing surfaces."

The inventions disclosed and taught herein are directed to an implantable blood pump having improved magnetic flux properties.

SUMMARY OF THE INVENTIONS

An implantable blood pump, with improved efficiency, comprising, a rotatable impeller comprising a rotor core having a channel aligned along its longitudinal core axis; a core material within the longitudinal channel; a plurality of substantially radially-oriented channels configured to extend from the longitudinal channel outwardly; and a magnetic material within each of the radially-oriented channels, the magnetic material and the core material in magnetic flux communication.

BRIEF DESCRIPTION OF THE SEVERAL VIEWS OF THE DRAWINGS

The following figures form part of the present specification and are included to demonstrate certain aspects of the present invention. The invention may be better understood by reference to one or more of these figures in combination with the detailed description of specific embodiments presented herein.

Figure 1:
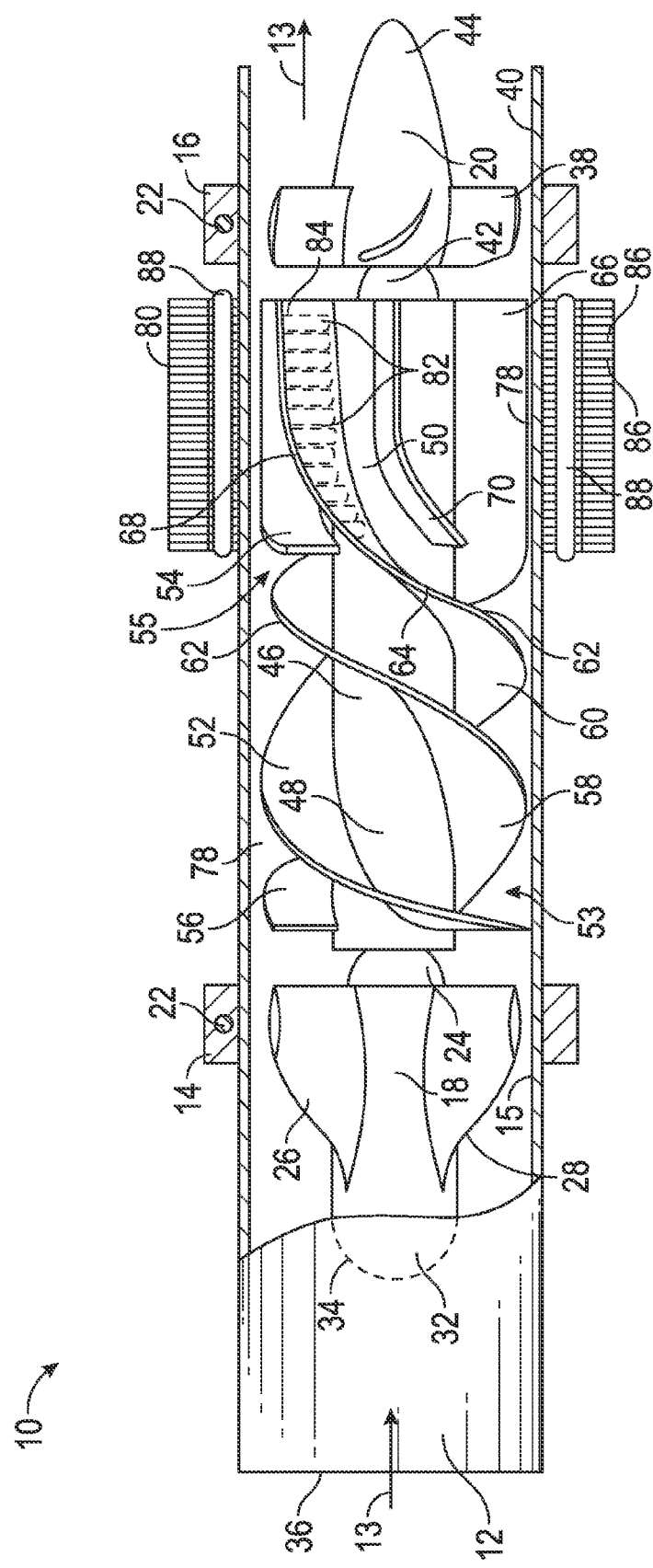
FIG. 1 is from U.S. Pat. No. 5,527,159, and illustrates an implantable blood pump according to the prior art.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DETAILED DESCRIPTION

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications is and alternative forms. Lastly, the use of a singular term, such as, but not limited to, "a," is not intended as limiting the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Particular embodiments of the invention may be described below with reference to block diagrams and/or operational illustrations of methods. It will be understood that each block of the block diagrams and/or operational illustrations, and combinations of blocks in the block diagrams and/or operational illustrations, can be implemented by analog and/or digital hardware, and/or computer program instructions. Such computer program instructions may be provided to a processor of a general-purpose computer, special purpose computer, ASIC, and/or other programmable data processing system. The executed instructions may create structures and functions for implementing the actions specified in the block diagrams and/or operational illustrations. In some alternate implementations, the functions/actions/structures noted in the figures may occur out of the order noted in the block diagrams and/or operational illustrations. For example, two operations shown as occurring in succession, in fact, may be executed substantially concurrently or the operations may be executed in the reverse order, depending upon the functionality/acts/structure involved.

Assignee Reliant Heart Inc., through its predecessors, is the licensee under U.S. Pat. No. 5,527,159; U.S. Pat. No. 5,947,892; and U.S. Pat. No. 5,957,672, and other patents. For all purposes of this application, the text and figures of U.S. Pat. No. 5,527,159; U.S. Pat. No. 5,947,892; and U.S. Pat. No. 5,957,672 are incorporated herein as if fully set forth.

We have invented an implantable blood pump having improved magnetic flux properties. Referring to the FIG. 1, a conventional impeller design with magnets located in the drive section of the blades is shown. In this design, the magnets are placed in the blades and do not extend into the hub portion of the impeller.

More specifically, as explained in U.S. Pat. No. 5,527,159, there is a shown a rotary blood pump 10 in accord with the present invention. Blood pump 10 includes a preferably metallic tubular pump housing 12 which is, in a preferred embodiment, a straight-sided cylinder. Pump housing 12 has a smooth inner bore wall 15 to minimize thrombus formation. Pump housing 12 defines a blood flow path 13 therethrough in the direction indicated by blood flow arrows shown in FIG. 1. Front and rear clamps 14 and 16, respectively, are used to secure flow straightener 18 and diffuser 20 within pump housing 12.

Flow straightener 18 serves two basic functions: (1) it straightens blood flow to reduce hemolysis while improving pump efficiency, and (2) it provides a support structure for front ball-socket bearing assembly 24, as discussed hereinafter. By straightening the flow of blood as it initially flows into the entrance 36 of pump 10, hydraulic efficiency is increased. Flow straightener 18 preferably has a number of fixed blades 26, but could have only two blades. For purposes of lowering thrombosis, the front edge 28 of each blade 26 is sloped from inner housing wall 15 to flow straightener hub 32 so that blood trauma by contact with blades 26 is minimized. Also to reduce blood trauma, flow straightener hub 32 is cylindrical with a round leading surface 34.

Diffuser 20 also has two basic purposes: (1) it de-accelerates and redirects the outflow at blood flow path exit 40 axially to boost pump performance, and (2) it serves as a support structure for the rear rotor bearing 42. Blades 38 are fixably engaged with pump housing 12 after rear clamp 16 is tightened by screw 22.

Rotor 46 is supported for rotary movement with pump housing 12 by front and rear bearings 24 and 42, respectively. Rotor 46 is divided into two portions along its is axis based on the type and function of the blades disposed thereon. Inducer portion 48 is disposed in the front part of rotor 46, i.e., nearer to the pump inlet 36. Impeller portion 50 is disposed in the rear part of rotor 46 closer to pump outlet 40.

Inducer blades 52 on inducer 53 have a variable pitch along their axial length. The inducer blades 52 pre-rotate the blood before it enters the main pumping or impeller 54 to reduce hemolysis. A shallow entrance angle of leading end 56 of inducer blade 52 effectively engages the blood for movement without damaging the blood. The pitch of inducer blade 52 continues to change along its axial length, through a midpoint 58 of the blade to the tailing end 60 of inducer blade 52. Pump 10 includes an interconnecting blade portion 62.

Impeller blades 54 on impeller 55 have an entrance angle in leading end region 64 that preferably smoothly tapers to an outlet angle at blade tailing end region 66. Impeller blades 54 include axially longer impeller blades, such as longer blade 68, and axially shorter impeller blades, such as shorter blade 70. There is a radial clearance 78 between inducer 53 and/or impeller 55 with respect to the pump housing inner wall 15.

In order to reduce the air gap between stator 80 and magnets 82, the magnets are preferably sealingly mounted within impeller blades 54. Each magnet 82 is encapsulated in an individual pocket 84. Field winding 88 generates a magnetic field to rotate rotor 46. Stator 80 is comprised of individual stator laminations 86.

Referring to FIGS. 2-6, a prior art impeller may be modified and improved in accordance with the inventions disclosed herein to allow additional magnetic material and/or other materials into the impeller or rotor core to improve the magnetic flux properties. Additionally or alternately, the impeller or rotor is configured to facilitate magnetic flux passing through the core, such as by having all impeller blade magnets in contact with the core material. These design improvements increase magnetic flux of the impeller and improve pump efficiency.

Figure 2:
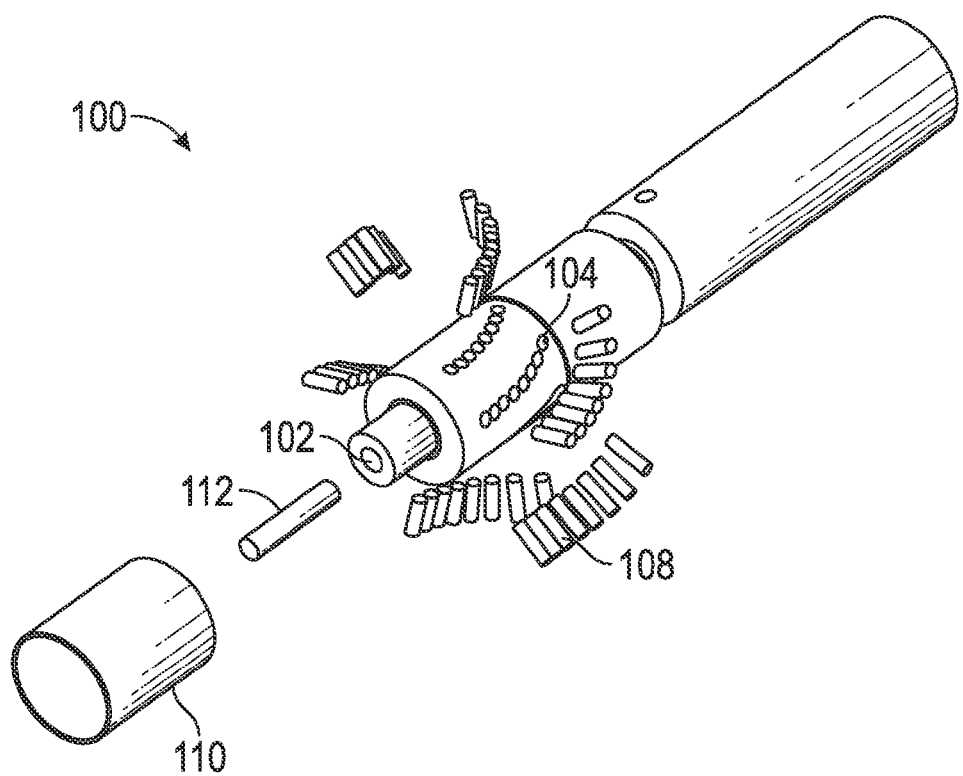
FIG. 2 illustrates a rotor core according to the present inventions.
Figure 5:
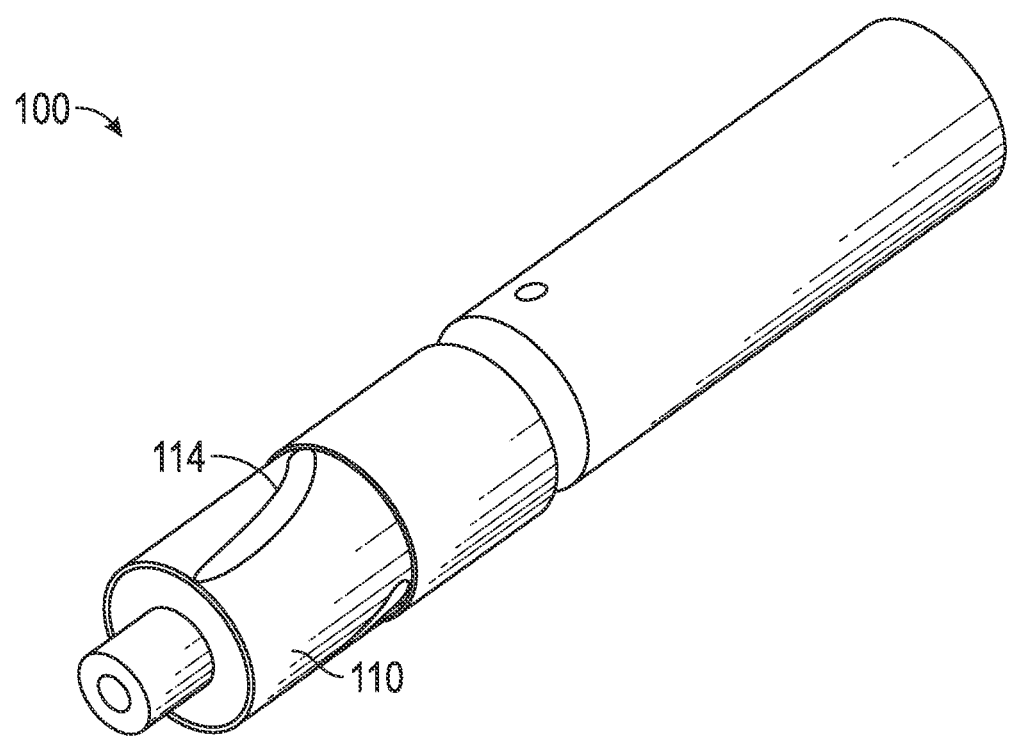
FIG. 5 illustrates a rotor core of according to the present inventions.
Figure 6:
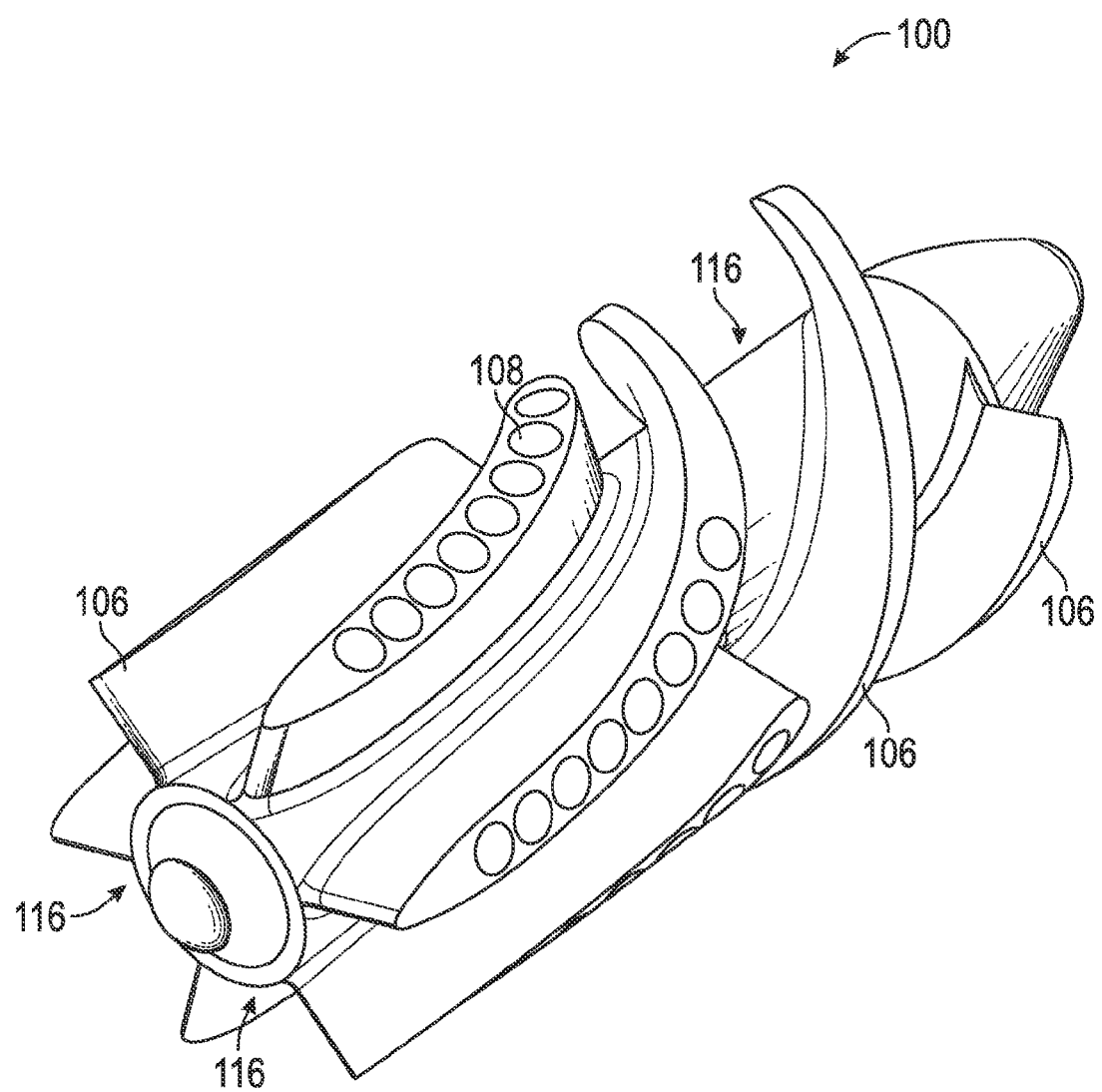
FIG. 6 illustrates one of many possible embodiments of a rotor according to the present inventions.

It is preferred, although not required, that the impeller of the present invention be formed as illustrated in FIG. 6, by machining impeller blades from a rotor core configured according to the inventions described herein. As illustrated in FIG. 2, a rotor core 100 may have an axial channel 102, hole, bore or slot formed through the center of the rotor core 100. A plurality of radial channels 104, holes, bore or slots may also be formed in the rotor core 100, such as by drilling, from the outer diameter of the rotor core 100 to the axial bore 102. These radial channels 104 preferably follow the outer diameter contour of the impeller blades 106. Preferably, the radial bores 104 are filled with a magnetic material 108. For example, and without limitation, if the radial channels 104 are configured as cylindrical bores, cylindrical magnets 108 may be fit, such as, interference fit into the cylindrical radial bores 104. Even if an interference fit is used, it is preferred that a sleeve 110 is placed over the exposed radial channels 104 and the interface between the channels 104 and the sleeve 110 is preferably welded to ensure that the magnets 108 cannot dislodge or move during use of the pump. See FIG. 5.

The central channel 102 may be filled with a material 112 (magnetic or not) configured to allow for magnets 108 in the radial channels 104 of opposite polarity to communicate magnetic flux. As for the central channel material 112, it may comprise iron, copper, neodymium, a polymer, air or a combination thereof. Preferably, the core material 112 is configured to pass magnetic flux, or augment the communication of magnetic flux through the center portion of the impeller/rotor core from one radial magnet to the other. Preferably, the north and south poles are positioned next to each other in the bottom of the radial channels 104, also the magnets directly across the center channel from each other are placed so that the north pole of one magnet faces the south pole of the other. Preferably, the core material 112 is sized to make and maintain intimate contact with each of the magnets 108 in the radial channels 104.

By providing an impeller core 112 that communicates magnetic flux from one radial magnet 104 to the other, the strength of the magnets is effectively increased by reducing or eliminating the flux blockage in the middle of the impeller.

It is preferred that the radial magnets 104 extend from about the outer surface into the rotor core so that each magnet 104 reaches the center channel 102. This configuration allows the magnets in each neighboring channel to positively affect the magnet next to it.

It is preferred to minimize the distance from the top of each radial magnet to the impeller blade tip, i.e., out impeller surface. This configuration reduces the loss of power caused by any gap between the motor stator and the impeller.

In one of many possible embodiments, it is preferred that the impeller be fabricated from the following materials. The rotor core is preferably 6AL4V titanium (ASTM Grade 5). The radial magnets are Neodymium Iron Boron. The center channel material preferably is iron or a lightweight polymer.

Figure 3:
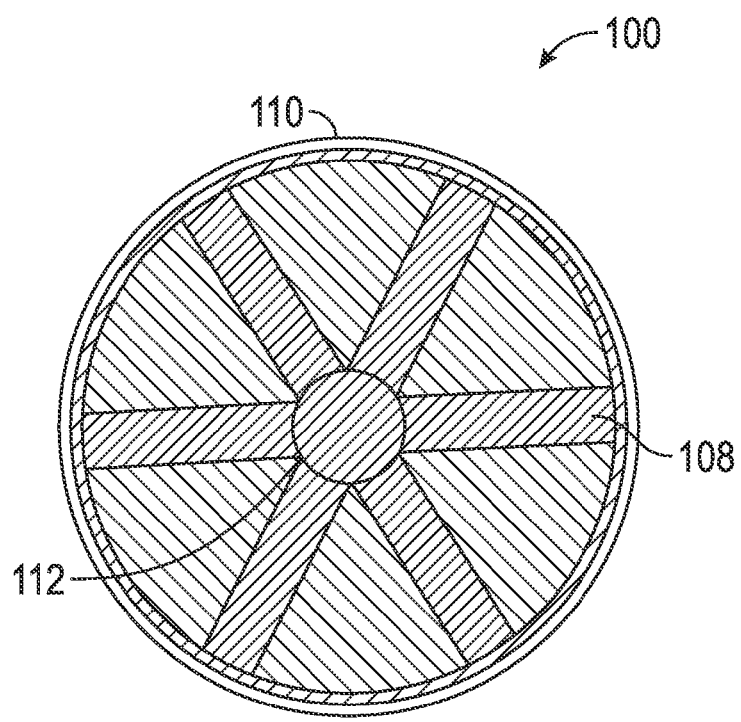
FIG. 3 illustrates a transverse cross sectional view of a rotor core according to the present inventions.
Figure 4:
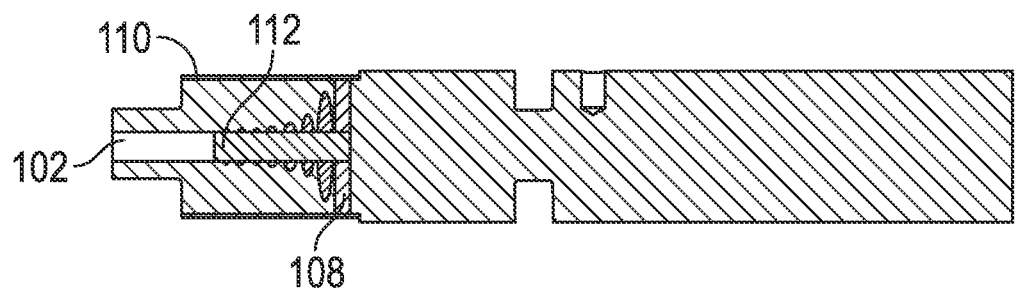
FIG. 4 illustrates a longitudinal cross sectional view of a rotor core according to the present inventions.

FIG. 3 shows the rotor core 100, assembled with the magnets 108, sleeve 100, and core material 112 in place. The blades 106 may then be formed by machining channels 116 therebetween. See FIG. 6. As shown in FIG. 5, the sleeve 110 is preferably attached with continuous welds 114 that follow the profile of each blade 106, such that when channels 116 between the blades 106 are machined away, the sleeve 110 forms a solid cap which completely covers and hermetically seals the magnets 104 within the blades 106. Due to the continuous nature of the cap which has been created, the O. D. of the impeller may be reduced to a final diameter that is minimally larger than the diameter formed by the magnets 104 to allow the magnetic gap between the magnets 104 and the stator to be optimized for purposes of building an efficient electric motor without compromising seal which prevents the magnetic is material from coming into contact with blood.

Once the impeller or rotor core 100 is fabricated, including welding the radial magnets 104 as shown in FIG. 5, the impeller may be fabricated by machining the impeller blades 106 out of the core body. A finished impeller is illustrated in FIG. 6, although the circular magnet ends are shown for location only and not visible because of the welded sleeve.

Other and further embodiments utilizing one or more aspects of the inventions described above can be devised without departing from the spirit of Applicant's invention. For example, while the radial magnets are shown in only a portion of the blade assembly, the magnets could extend the entire length of the blades. Also, rather than machining the blades from the rotor core, blades with integral magnets can be attached to a hub body. Further, the various methods and embodiments of the methods of manufacture and assembly of the system, as well as location specifications, can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

What is claimed is:

1. An implantable blood pump, comprising:
   a rotatable impeller comprising a rotor core having a longitudinal axis, the rotor core comprising a first material and a channel aligned substantially along the longitudinal core axis;
   a core material, different from the first material, within the longitudinal channel;
   a plurality of substantially radially-oriented channels configured to extend from the longitudinal channel outwardly; and
   a magnetic material within each of the radially-oriented channels, the magnetic material and the core material in magnetic flux communication.

2. The blood pump of claim 1 wherein the radially-oriented channels extend along blades of the impeller.

3. The blood pump of claim 1 wherein the radially-oriented channels are capped by a sleeve.

4. The blood pump of claim 1 wherein a weld secures a sleeve over the radially-oriented channels.

5. The blood pump of claim 1 wherein a first magnetic material in a first one of the radially-oriented channels aligned in a first blade is in magnetic flux communication with a second magnetic material in a second one of the radially-oriented channels aligned in a second blade through the core material.

6. The blood pump of claim 1 wherein a first plurality of the radially-oriented channels is aligned along a first blade and a second plurality of the radially-oriented channels is aligned along a second blade.

7. The blood pump of claim 6, wherein the blades are of varying pitch along their length.

8. The blood pump of claim 1 wherein the core material is magnetic.

9. The blood pump of claim 1 wherein the core material is non-magnetic.

10. The blood pump of claim 1 wherein the core material is titanium.

11. The blood pump of claim 1 wherein the core material is iron.

12. The blood pump of claim 1 wherein the core material is a polymer.

13. The blood pump of claim 1 wherein the magnetic material is Neodymium Iron Boron.

14. The blood pump of claim 1 wherein a north pole of the magnetic material in one of the radially-oriented channels is positioned next to a south pole of the magnetic material in an adjacent one of the radially-oriented channels.

15. The blood pump of claim 1 wherein a north pole of the magnetic material in one of the radially-oriented channels is positioned across from a south pole of the magnetic material in the radially-oriented channel on an opposite side of the rotor core.

16. The blood pump of claim 1 wherein the core material is in physical contact with the magnetic material in the radially-oriented channels.

17. An implantable blood pump, comprising:
    a rotatable impeller comprising a rotor core having a longitudinal axis and a plurality of blades extending outwardly from the rotor core,
       the rotor core comprising a rotor material and having a central channel aligned substantially along the longitudinal axis;
    a core material, different from the rotor material, within the central channel;
    a plurality of substantially radially-oriented channels along each blade and extending from the central channel outwardly; and
    a magnetic material within each of the radially-oriented channels, the magnetic material and the core material in physical communication.

18. The blood pump of claim 17 wherein a north pole of the magnetic material in one of the radially-oriented channels is positioned next to a south pole of the magnetic material in an adjacent one of the radially-oriented channels.

19. The blood pump of claim 17 wherein a north pole of the magnetic material in one of the radially-oriented channels is positioned across from a south pole of the magnetic material in the radially-oriented channel on an opposite side of the rotor core.

* * * * *